(12) United States Patent
Miller (10) Patent No.: US 9,492,016 B2
(45) Date of Patent: Nov. 15, 2016

(54) COMPACT, PORTABLE ELEVATING DEVICE FOR A LOWER LIMB

(76) Inventor: Bryan Miller, Woodland, CA (US)

( * ) Notice: Subject to any disclaimer, the term of this patent is extended or adjusted under 35 U.S.C. 154(b) by 924 days.

(21) Appl. No.: 13/315,164

(22) Filed: Dec. 8, 2011

(65) Prior Publication Data

US 2012/0312306 A1 Dec. 13, 2012

Related U.S. Application Data

(60) Provisional application No. 61/420,863, filed on Dec. 8, 2010.

(51) Int. Cl.
*A47C 16/00* (2006.01)
*A47C 16/02* (2006.01)

(52) U.S. Cl.
CPC .................................. *A47C 16/025* (2013.01)

(58) Field of Classification Search
CPC ...... A61G 13/00; A61G 13/10; A61G 13/12; A61G 13/1205; A61G 13/125; A61G 15/00; A61G 15/005; A61G 15/10; A61G 15/12; A61F 5/00; A61F 5/37; A61H 2201/00; A61H 2201/16; A61H 2201/1602; A61H 2201/164
USPC .............. 135/65–69, 71–75; 248/125.8, 155, 248/155.5, 188; 297/4–6; 602/5, 16, 23, 26; 628/28; 482/75–77, 79–80; 128/845
See application file for complete search history.

(56) References Cited

U.S. PATENT DOCUMENTS

| | | | |
|---|---|---|---|
| 3,696,826 A | 10/1972 | Gruzalski | |
| 4,776,108 A | 10/1988 | Bayless | |
| 5,261,699 A | 11/1993 | Marston | |
| 5,300,016 A | 4/1994 | Marlatt | |
| 5,318,068 A | 6/1994 | Haugen | |
| 5,735,303 A | 4/1998 | Cole | |
| 6,712,781 B1 | 3/2004 | Sheppard | |
| 6,799,592 B1 | 10/2004 | Reynolds | |
| 6,837,862 B2 | 1/2005 | Driver, Jr. | |
| 7,600,524 B2 | 10/2009 | West | |
| 2004/0049135 A1 | 3/2004 | Callanan et al. | |
| 2006/0217648 A1* | 9/2006 | Rogachevsky | ................. 602/20 |

FOREIGN PATENT DOCUMENTS

FR 2643813 A1 3/1989

* cited by examiner

*Primary Examiner* — Tarla Patel
(74) *Attorney, Agent, or Firm* — Temmerman Law Office; Mathew J. Temmerman (57) ABSTRACT

A device and method for maintaining a user's legs in an elevated position is presented. In particular, the embodiments comprise a base plate having a front surface and a rear surface, a calf cup and heel cup integrated with the front surface, a plurality of retractable leg members, a plurality of hinges, an attachment means comprising preferably a plurality of hook and loop fasteners, and a plurality of gripping caps. The base plate is adaptable to attach with the user's leg or footwear. The plurality of retractable leg members is adaptable to operate in a deployed configuration allowing the user's leg to rest thereon and/or in a stored configuration wherein the leg members become parallel with the rear surface of the base plate, and a locking mechanism is presented.

7 Claims, 9 Drawing Sheets

COMPACT, PORTABLE ELEVATING DEVICE FOR A LOWER LIMB

RELATED APPLICATION

This application claims priority from U.S. provisional application with Ser. No. 61/420,863, and which was filed on Dec. 8, 2010. The disclosure of the provisional application is incorporated herein as if set out in full.

BACKGROUND OF THE DISCLOSURE

Technical Field of the Disclosure

The present invention relates in general to leg support devices. More specifically, the invention relates to a leg support device adaptable to lock and maintain a user's leg in an elevated position, yet be carried discretely on the leg while the user moves.

Description of the Related Art

A wide variety of leg support devices have been developed for individuals suffering from leg injuries and recovering from leg surgeries. Crutches, canes and walkers are commonly used devices that provide body support and stability while a user is walking or standing on an injured leg or foot. For many leg injuries it is important from a medical standpoint when not walking to keep the leg or legs elevated. Elevation of the legs improves blood circulation, promotes healing and frequently lessens discomfort and pain by reducing the swelling associated with the injured muscles.

A common practice to elevate an injured or recovering leg while sitting in a chair or on a sofa is to prop the limb on available furniture or other stationary objects such as stools, coffee tables, desks, and other chairs. However, this solution suffers from two drawbacks. The first issue is that the stationary objects may not to be the correct height and so the user may have to to adjust their height relative to the objects. This causes the user to sit in an awkward position and may result in muscle strain.

Another issue regarding the use of a stationary object is lack of portability. It is frequently the case that for a given chair or sofa where the user may find himself or herself sitting, no stationary object such as a stool or coffee table is located conveniently nearby. In a home this may necessitate moving heavy objects around the house, which could exacerbate the injury to be healed and potentially cause additional injuries. This is even more problematic outside the home where, for example, many waiting rooms contain only banks of immovable chairs, presenting no objects on which to elevate the injured or recovering leg. Furthermore, it would not be practical for an individual using crutch to carry any sort of collapsible leg support.

Many attempts have been made to develop portable leg supporting devices. An early attempt is U.S. Pat. No. 3,696,826 issued to Gruzalski on Oct. 10, 1972, which provides a device for supporting an individual's leg in a substantially horizontal position when the individual is seated. The device includes a generally U-shaped ankle engaging member adapted to be secured around the user's ankle or lower calf, and a stanchion rotatably connected to the ankle-engaging member. The stanchion includes a pair of parallel support bars, each of which mounts the ankle-engaging member at one end thereof. The device is particularly designed to support a leg in a cast, and is adapted to be worn on the cast around the user's leg when the device is not in use. However, this device does not allow the user to sit in various positions that are comfortable for the user since the support bars are not easily height adjustable nor independently adjustable. Further, the device is not configurable such that the user may lock it into position with the weight of the elevated leg.

U.S. Pat. No. 6,712,781 issued to Sheppard on Mar. 30, 2004 presents a self-contained limb and cast support device to elevate a broken or sprained limb. This device is portable and can be converted to a position where it is less in the way while the user moves about. However, the hinges of the Sheppard device are placed on the sides of user's legs and in a position where they are likely to be caught on objects as the user walks and moves around. Thus, the device impedes walking or other basic motions of the user. Additionally, like the other prior art the device is not configurable such that the user may lock it into position with the weight of the elevated leg, nor are the legs of the device adjustable independently.

Hence, it can be seen that there is a need for a leg support device that is adaptable to easily attach to a user's leg or footwear thereby enabling the user to have easy access to the leg support at any time, in any location. Further, such a device would not get caught on other objects when the user performs basic body movements such as walking. Such a leg support device would not impede walking or other basic motions of the user. Such a leg support device should be readily adjustable individually to any desired height for providing sufficient elevation to the legs. Further, such a leg support device should be designed to extend in different lengths so that the user can tilt his foot either to the left or right according to the user's desire. Still further, such a leg support device should be easily and quickly attachable to modern orthotic footwear, commonly made of hard plastic, rather than cloth or softer materials. Such a leg support device would work in multiple configurations and should be lockable in each configuration. Finally, the device must be comfortable to wear, discrete, portable and fabricated from lightweight materials.

SUMMARY OF THE DISCLOSURE

The preferred embodiment provides a portable leg support device adaptable to maintain a user's legs in an elevated position.

The preferred embodiment is designed to attach to a leg or footwear and comprises a base plate having a front surface and a rear surface, the front surface comprising a calf cup and a heel cup, a plurality of retractable leg members connected to the rear surface, a plurality of hinges to attach the plurality of retractable leg members with the rear surface, an attachment means to attach the leg support device to the user's leg or footwear, and a plurality of gripping caps to provide proper grip to the floor from the plurality of retractable leg members to which they are attached. The base plate is adaptable to easily attach to or remove from, the user's leg or footwear. The plurality of retractable leg members is adaptable to operate in a deployed configuration and in a stored configuration. The deployed configuration maintains the user's leg in an elevated position. In the stored configuration, the plurality of retractable leg members becomes parallel with the base plate to allow the user to perform body movements without removing the leg support device.

The plurality of hinges prevents the plurality of retractable leg members from swinging between configurations as the user moves about and performs body movements in the stored configuration. The plurality of retractable leg members may be locked within the plurality of hinges in the deployed configuration such that the user's leg and/or footwear may be maintained in an elevated position. The attachment means is preferably a plurality of hook and loop fasteners that securely mounts the leg support device on the user's leg or footwear. The stored configuration configures the plurality of retractable leg members in a parallel position with the base plate that enables the user to perform body movements while wearing the leg support device.

In another aspect of the present invention, a method in accordance with the present invention is a method for maintaining a user's leg in an elevated position utilizing a leg support device.

A first objective of the present invention is to provide a leg support device that when attached to a leg or footwear, the device does not impede walking or other basic motions.

Yet another objective of the present invention is to provide a leg support device that may be quickly and easily converted from a stored configuration to a deployed configuration thereby allowing the instant access of the leg support device in any location.

Yet another object of the present invention is to provide a leg support device that may be quickly and easily attached and detached from a leg and/or footwear.

A further objective of the present invention is to provide a leg support device that is readily adjustable to any desired height.

A still further objective of the present invention is to provide a leg support device that may be locked in a deployed configuration by the weight of the user's own leg.

These and other advantages and features of the present invention are described with specificity so as to make the present invention understandable to one of ordinary skill in the art.

BRIEF DESCRIPTION OF THE DRAWINGS

In order to enhance their clarity and improve understanding of these various elements and embodiments of the invention, elements in the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

Figure 1:
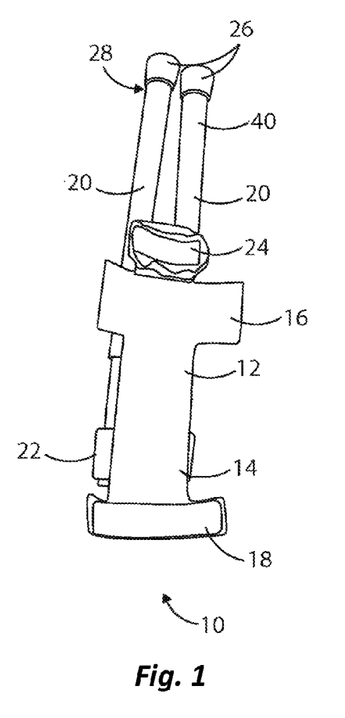
FIG. 1 is a perspective view of a leg support device in accordance with the an embodiment of the present invention.

Turning now to the drawings, FIG. 1 is a perspective view of a leg support device 10 for maintaining a user's legs in an elevated position. The leg support device 10 comprises a base plate 12 having a front surface 14 and a rear surface 32 (shown in FIG. 3), a calf cup 16 and heel cup 18 integral with the front surface 14, a plurality of retractable leg members 20 connected to the rear surface 32 (FIG. 3) and having a bottom portion 28 to facilitate the height adjustment of the plurality of retractable leg members 20, a plurality of hinges 22 to attach the plurality of retractable leg members 20 with the rear surface 32 (FIG. 3), an attachment means 30 (FIG. 3) attached with the rear surface 32 to attach the leg support device 10 to the user's leg or footwear, and a plurality of gripping caps 26 preferably comprising rubber to provide proper grip to the plurality of retractable leg members 20. The gripping caps 26 provide a nonslip surface for the legs and also prevent scratching on hardwood floors.

The attachment means 30 (shown in FIG. 3), is a plurality of hook and loop fasteners although straps, ties and other flexible means of attachment may be employed.

Continuing with FIG. 1, base plate 12 is adaptable and shaped to easily attach to the back of a user's leg or footwear. There are various means of attachment, but in a preferred embodiment hook and loop fasteners are used both on the front surface 14 of the base plate 12 and on the rear surface of a piece of footwear, such as an orthotic boot. Hook and loop fasteners are preferred because the ease of connection and disconnection allows the leg support device 10 to be easily and quickly attached to footwear, or removed if need be. Hook and loop fasteners are also preferred because in general the components of the present invention and the components of modern orthotic boots are hard plastic like materials, rather than flexible boots that have been used in the past. Other more permanent attachment means may be used, such as glue or rivets. Finally, and as described in more detail below the leg support device 10 may be a permanent component to an orthotic boot and built by a boot manufacturer. Because of the rigidity of base plate 12, it may even serve as a structural component in a manufactured orthotic boot. The downside to this embodiment is that the device is not easily releasable or detachable.

In all embodiments, none of the plurality of hinges 22 are positioned in a location lateral to the side of the knee. This placement in important to prevent said plurality of hinges 22 from bumping against or catching on objects as the user walks. The calf cup 16 optionally includes a foam pad 24 attached thereon, and best depicted in FIG. 4. In other embodiments, the entire front surface 14 or varying amounts of front surface 14 may be covered with a foam pad (not shown).

Figure 6:
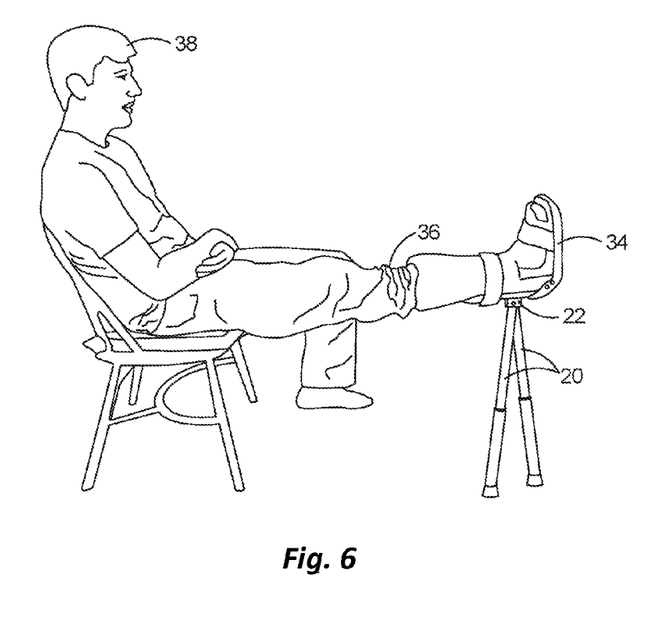
FIG. 6 is a perspective view of an embodiment of the invention, illustrating a user in a sitting position by keeping the leg in an elevated position utilizing the leg support device.

Turning briefly to FIG. 6, the plurality of retractable leg members 20 is adaptable to operate in a deployed configuration that allows the user's leg 36 to be in an elevated position and in a stored configuration in which the plurality of retractable leg members 20 becomes parallel with the base plate 12 that allows the user to perform body movements (See FIG. 9) without removing the leg support device 10. The leg support device 10 secures the user's leg in different elevations by adjusting the height of the plurality of retractable leg members 20.

Figure 2:
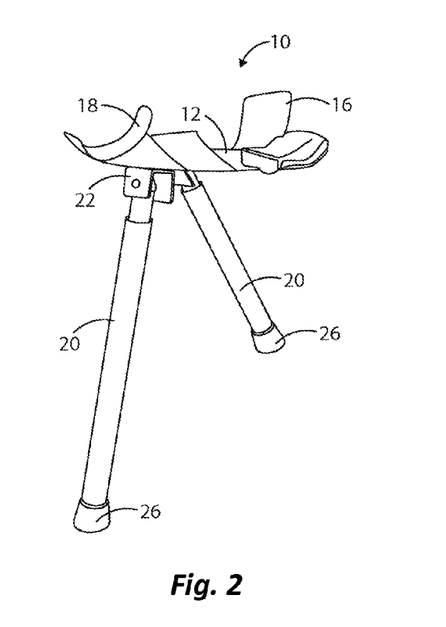
FIG. 2 is a perspective view of an embodiment of the present invention, illustrating the leg support device in a deployed configuration.

FIG. 2 shows a second perspective view of the leg support device 10, illustrating the leg support device 10 in a deployed configuration. In this embodiment, simple hinges are used for ease of manufacturing and reduction of cost. Improved hinges are shown in later embodiments. In all embodiments, the deployed configuration is achieved by manually rotating through their hinge the plurality of retracting leg members 20 such that the members are generally perpendicular with the back of the leg support device 10, as shown here. The user may then firmly place the leg support device 10 on a surface utilizing the plurality of gripping caps 26. The plurality of retractable leg members 20 may be locked within the plurality of hinges 22 in the deployed configuration that allows the user to maintain the user's leg or footwear in the elevated position. There are various known hinge locks in the industry, and while one in particular is shown in later embodiments, other suitable locks may be utilized. The plurality of retractable leg members 20 may be made of material selected from a group consisting of aluminum, steel and plastic. Each of the gripping caps 26 is attached to the bottom portion 28 of each of the plurality of retractable leg members 20. The gripping caps 26 increase friction between the bottom portion 28 and the surface on which the user 38 (FIG. 6) rests his or her leg, and further serve to protect that surface from scratches.

Continuing with FIG. 2, in this embodiment, the height adjusting mechanism is a telescopic mechanism. In other embodiments a button lock system may be used, and other conventional means of temporarily locking an extending leg member may be used. The plurality of retractable leg members 20 is designed to extend independently so that the leg members 20 reach different heights and provide a comfortable sitting position to the user 38. Since the plurality of retractable leg members 20 is attached at the rear surface 32 of the base plate 12, the device 10 is less likely to be caught on other objects when the user 38 performs even basic body movements such as walking. Preferably, the attachment point of said plurality of retractable leg members is such that width of said plurality of hinges (when taken as a viewpoint shown best in FIG. 10A) is now wider than the width of said base plate 12. That is, base plate 12, defined as elongate and shown as such in FIG. 10A, also has a longitudinal width, and the width of said plurality of hinges 22 is no wider than said longitudinal width.

Figure 3:
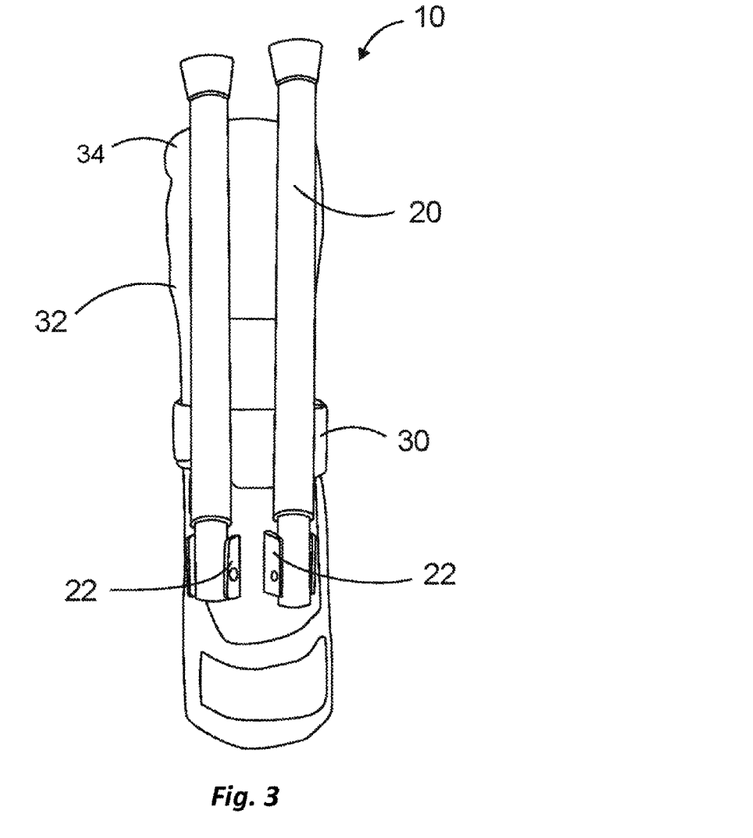
FIG. 3 is a perspective view of an embodiment of the invention, illustrating the leg support device in a stored configuration.
Figure 9:
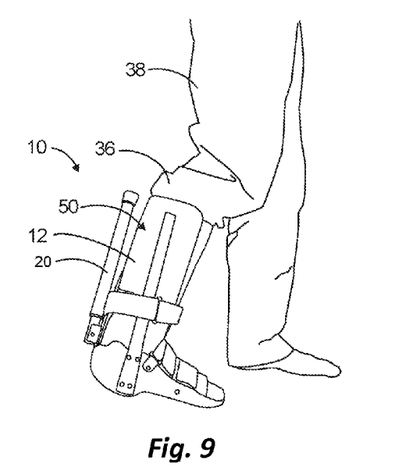
FIG. 9 is a perspective view of an embodiment of the invention, illustrating the user in a standing position by wearing the leg support device.

FIG. 3 illustrates the leg support device 10 attached to a piece of footwear 34 using the plurality of hook and loop fasteners 30. The plurality of hook and loop fasteners 30 securely mounts the leg support device 10 on the user's leg or footwear. Other suitable mounting means may be utilized. The stored configuration maintains the plurality of retractable leg members 20 in a position parallel with the base plate 12 that enables the user 38 to perform body movements while wearing the leg support device 10 (FIG. 9). The plurality of hinges 22 includes a mechanism for locking the device in one of either the deployed configuration or the stored configuration. The preferred locking mechanism is described later in this document.

Figure 4:
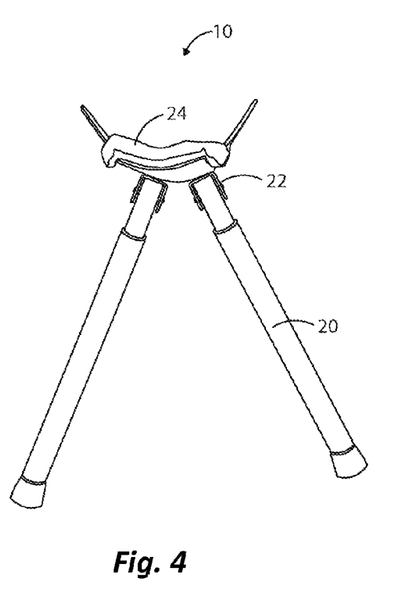
FIG. 4 is a perspective view of an embodiment of the invention.

FIG. 4 is a top view of the leg support device 10, illustrating the optional foam pad 24. The foam pad 24 provides increased comfort for the user and securely mounts the leg support device 10 on the user's leg or footwear. Notably, "user's leg" as defined in this application may include a bare leg or a leg with a layer of clothing around it, such as a sock and/or pant leg. This optional foam pad provides additional comfort when the device is not used with footwear, but instead used with either a bare or clothed leg. The base plate 12 includes a bent portion that allows the leg support device 10 to securely and comfortably mount on the user's leg or footwear. Preferably, the foam is flexible enough to accommodate the bent portion and therefore the user's leg. As discussed with regard to FIG. 1, the foam pad 24 is optional. The base plate 12 is designed as a curved structure to attach firmly to the user's leg or footwear. This curved structure distributes pressure from the user's leg evenly against the rear surface, increasing the comfort experienced by the user. The calf cup 16 and the heel cup 18 are curved in a same direction for the secure attachment to the user's leg or footwear.

Figure 5:
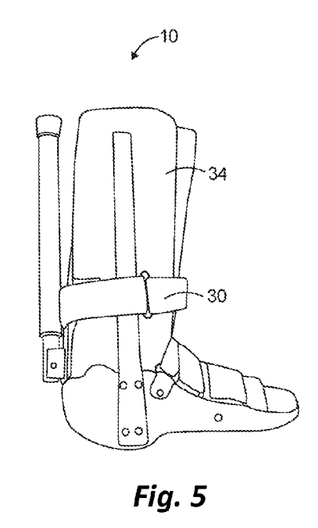
FIG. 5 is a perspective view of an embodiment of the invention, illustrating the leg support device attached with the footwear utilizing the hook and loop fasteners.

FIG. 5 is a perspective view of the preferred embodiment, illustrating the leg support device 10 attached with the footwear 34 utilizing the hook and loop fasteners 30. Here, the device is shown in the stored configuration, such as for when the user is walking around. This attachment makes the leg support device 10 ready for instant deployment without disrupting any basic body movements that would normally be associated with a person wearing the footwear. The footwear 34 is preferably an orthotic boot and preferably the device is an accessory for the orthotic boot.

In the preferred embodiment, the height adjusting mechanism is a telescopic mechanism. The plurality of retractable leg members 20 is designed to extend independently so that the leg members 20 may reach differing and independent heights therefore providing a comfortable sitting position to the user 38 (FIG. 6). Since the plurality of retractable leg members 20 is attached at the rear surface 32 of the base plate 12, the device 10 does not get caught on other objects when the user 38 (FIG. 6) performs body movements like walking.

FIG. 6 is a perspective view illustrating the user 38 in a sitting position by keeping the leg 36 in an elevated position utilizing the leg support device 10. The plurality of retractable leg members 20 utilizes a height adjusting mechanism to allow the user 38 to adjust the height of the plurality of retractable leg members 20 according to user's desire. As shown in FIG. 6, the plurality of legs may be extended. The pressure from the weight of the user's leg 36 presses the plurality of retractable leg members 20 downwards and locks the leg members 20 within the plurality of hinges 22. In this configuration, the plurality of retractable leg members 20 becomes approximately perpendicular to the base plate 12. When the user 38 pulls the plurality of leg members 20 away from the user's leg 36, the plurality of leg members 20 is unlocked and may be moved to stored configuration wherein they are generally parallel to the base plate 12. When the user 38 stands and/or walks, gravity tends to pull the plurality of retracting leg members 20 downwards and the leg members 20 become parallel with the base plate 12. Preferably, the weight of the leg members 20 alone when pulled in a perpendicular direction away from the user's leg (such as if the user 38 were to slightly lift the leg from the position as shown in FIG. 6) is not enough to unlock the legs so they may be moved from the deployed configuration to the stored configuration. Instead, it is preferred the user 38 be required to supply additional force in a direction perpendicular to the user's own leg. Once unlocked, the legs may swing freely between stored configuration and deployed configuration.

Figure 7:
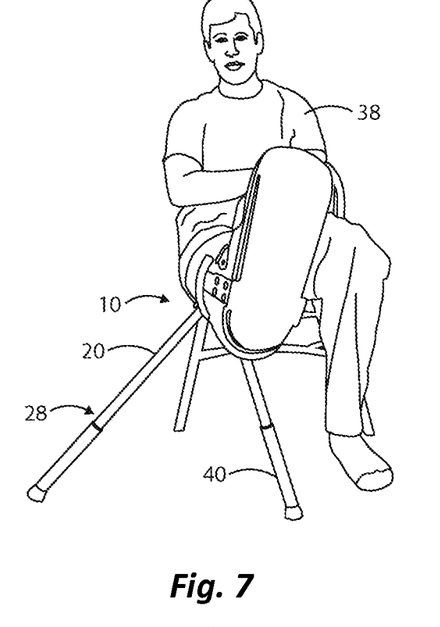
FIG. 7 is a perspective view of the preferred embodiment of the invention, illustrating the plurality of retracting leg members extended such that the user's foot is tilted inward.
Figure 8:
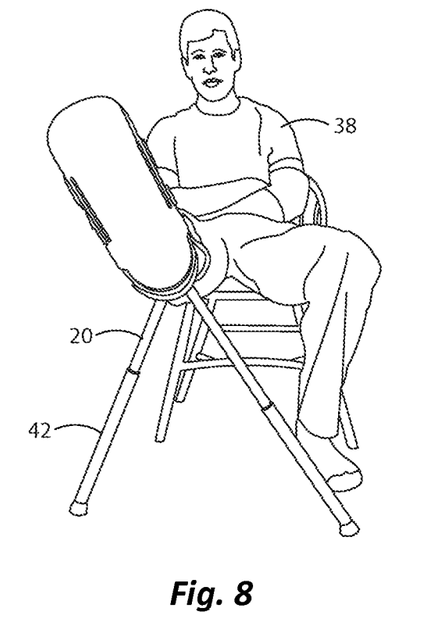
FIG. 8 is a perspective view of the preferred embodiment, illustrating the plurality of retracting leg members extended such that the user's foot is tilted outward.

Referring to FIG. 7, the plurality of retractable leg members 20 is extended independently so that the leg members 20 extend to varying lengths to provide a comfortable sitting position to the user 38. The leg members 20 may telescope in any fashion that is well known in the art. In one embodiment, the user 38 rotates the bottom portion 28 of one of the plurality of retractable leg members 20 relative to the upper part of the bottom portion 28. This allows the bottom portion of the leg members to slide downwards out of tube within the leg member 20. When the desired length is reached, the user rotates the bottom portion 28 in the opposite direction, thereby locking the one of the plurality of retractable leg members 20 in place. FIG. 7 and FIG. 8 together illustrate the effect of varying which retractable leg members 20 is shorter than the other. This has the effect of tilting the foot either inward (as in FIG. 7) or outward (as in FIG. 8). This tilting feature allows the user 38 to rest in various positions that are comfortable for the user 38, helping fight fatigue and stiffness that may occur from being in one single position for a long period of time.

FIG. 9 is a perspective view illustrating the user 38 in a standing position and wearing the leg support device. In the stored configuration, the plurality of retractable legs 20 is parallel with the base plate 12 and as noted above the hinges in all embodiments are not located lateral of the knee. This arrangement allows the user 38 to perform basic body movements like, walking without removing the leg support device 10 from the leg 36. Since the leg members 20 is attached at the rear surface 32 of the footwear, the device 10 does not get caught on other objects when the user 38 performs body movements.

Figure 10A:
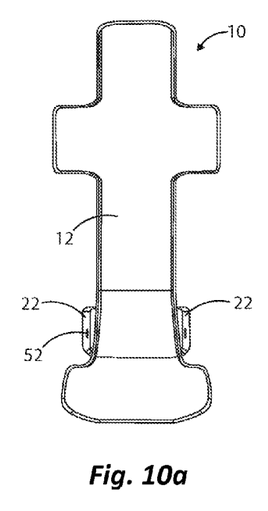
FIG. 10a is a front view of a front surface of a base plate of the leg support device according to the preferred embodiment of the invention and wherein the legs are removed for clarity.
Figure 10B:
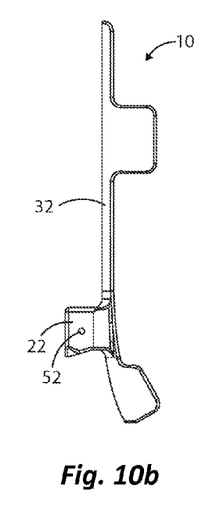
FIG. 10b is a side view of the base plate according to the preferred embodiment and where the legs are removed for clarity.
Figure 10C:
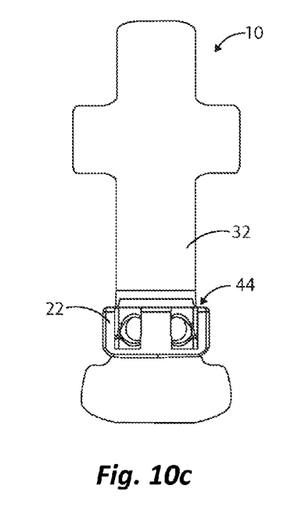
FIG. 10c is a rear view of the rear surface of the base plate of the preferred embodiment wherein the legs are removed for clarity of the hinge pockets.

FIGS. 10A through FIG. 10C show respectively, a front view, side view, and rear view of the base plate 12 according to the preferred embodiment of the invention, and illustrating the plurality of hinges 22 attached at the rear surface 32 of the base plate 12. Referring to FIG. 10A, each of the plurality of hinges 22 in this embodiment includes at least one pinhole 52. Each of said plurality of leg members also comprises a leg member pin slot 56 (not shown in this Figure). Pin 54 (removed for clarity from this figure) is threaded through both pinhole 52 and leg member pin slot 56, allowing each of said plurality of leg members to rotate about pin 54. That is, pin 54 serves as the axis about which the plurality of leg members may rotate. The top of pin 54 may be seen in FIG. 12, wherein the pin is threaded through both pinhole 52 and leg member pin slot 56, not labeled in this Figure.

Figure 11:
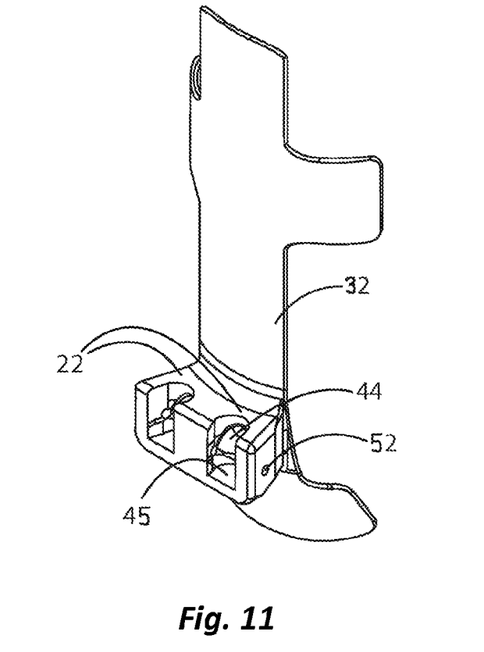
FIG. 11 is a perspective view of the rear surface according to the preferred embodiment with the legs removed for clarity, and illustrating the hinge pocket attached at the rear surface of the base plate.

Turning next to FIG. 11, a detailed view of rear surface 32 and the plurality of hinges 22 is shown. Specifically, pinhole 52 is again shown, through which pin 54 (not shown for purposes of clarity) may be threaded in order to secure the plurality of leg members (now shown). Importantly, FIG. 11 also depicts a plurality of first hinge pockets 44 and a plurality of second hinge pockets 45, which as explained below are used to secure said plurality of leg members. Two of said plurality of hinges are shown 22, however the hinge pockets are only labeled with references numbers for the right-most hinge depicted. Each of said plurality of first hinge pockets 44 is cavity, recess, or other suitable receptacle for nesting a portion of one of said plurality of leg members. Likewise, each of said plurality of second hinge pockets 45 is cavity, recess, or other suitable receptacle for nesting the same portion of one of said plurality of leg members.

As each of said plurality of leg members rotates about said pin 54, it may at certain points of rotation be slotted into either said hinge pocket. Once inserted into either said hinge pocket, the leg member is no longer free to rotate, and is instead locked from further rotation. The locking system allows the plurality of hinges 22 to lock the plurality of retractable leg members 20 between the stored configuration (when in one of said plurality of second hinge pockets 45) and the deployed configuration (when in one of said plurality of first hinge pockets 44). Because of the independent nature of the locks (that is, the entire plurality of hinges 22 need not be actuated together), the user 38 has the option of keeping fewer than the entirety of all retractable leg members 20 either in the deployed configuration or the stored configuration. For instance, while traveling on an airplane, a user may desire to deploy only one leg due to space issues or if there is a solid object against which to lean the user's leg.

Figure 15:
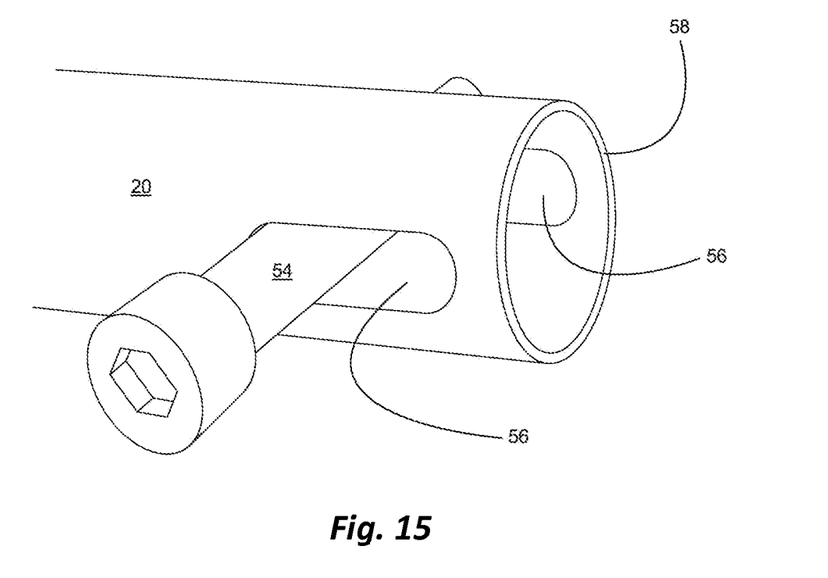
FIG. 15 is a detailed view of a hinge component in a locked configuration according to a preferred embodiment of the invention.
Figure 16:
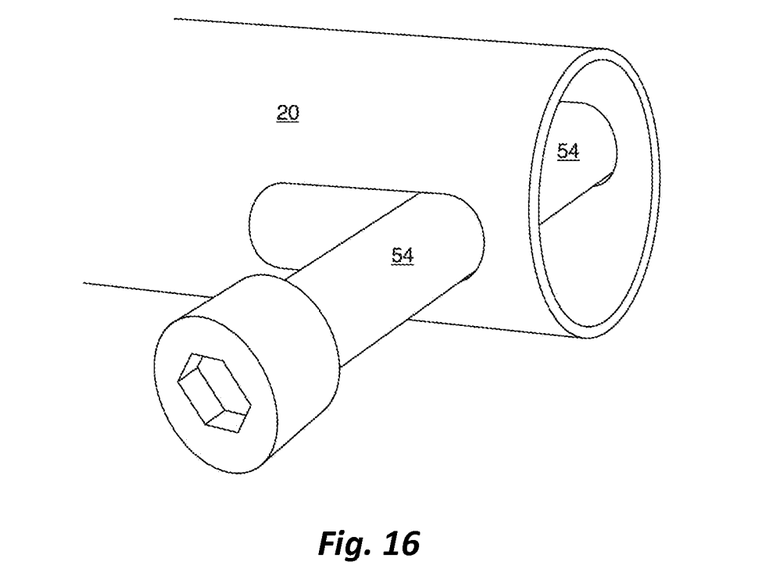
FIG. 16 is a detailed view of a hinge component in an unlocked configuration according to the preferred embodiment of the invention.

The communication between pin 54 and pin slot 56 is shown in detail in FIG. 15 and FIG. 16. Although the axis of rotation of each of said plurality of retractable leg members 20 is always pin 54, the relative position of the two is variable, dependent upon the precise relative location of pin 54 and pin slot 56, as shown best in a comparison of FIG. 15 and FIG. 16. FIG. 15 shows one of said plurality of leg members 20 in a locked position, either said deployed configuration or said stored configuration. Because the leg member tip 58 is nested in one of said hinge pockets (not shown in this figure), the leg member is not free to rotate.

Conversely, when the relative position of said pin 54 and said pin slot 56 is as shown in FIG. 16, the leg member is free to rotate.

In a preferred embodiment, when in the deployed configuration, the user 38 rests his or her leg 36 on the leg support device 10, thereby urging said plurality of retractable leg members 20 to remain nested in said plurality of second hinge pockets 46. As the user 38 removes the urging pressure, the downward weight of the plurality of retractable leg members 20 alone, as they are pulled by gravity generally perpendicularly from the rear surface 32 is sufficient to disengage the system from the deployed configuration such that the leg members may then be rotated freely as described above. No additional force is required by the user.

Figure 12:
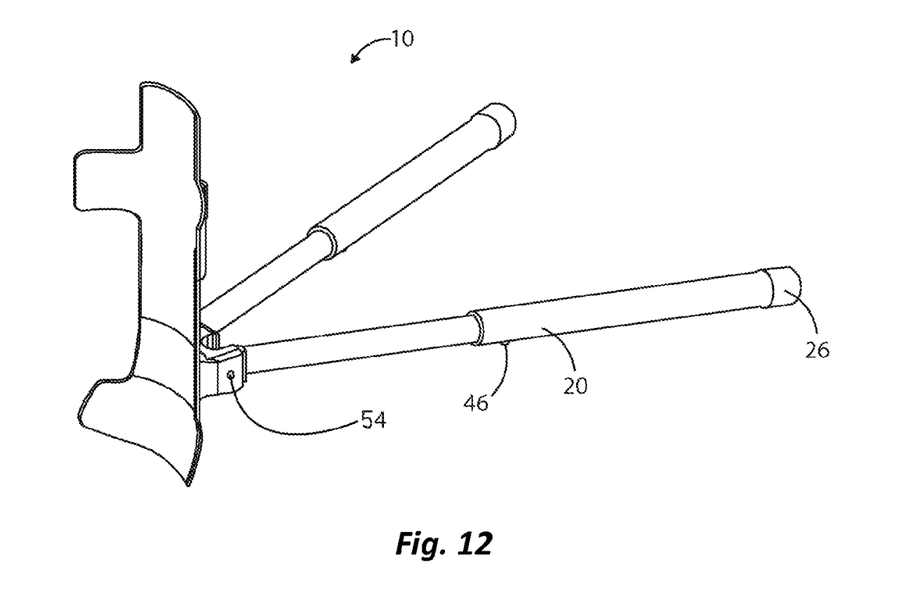
FIG. 12 is a perspective view of the preferred embodiment, illustrating the plurality of leg members in an extended position.
Figure 13:
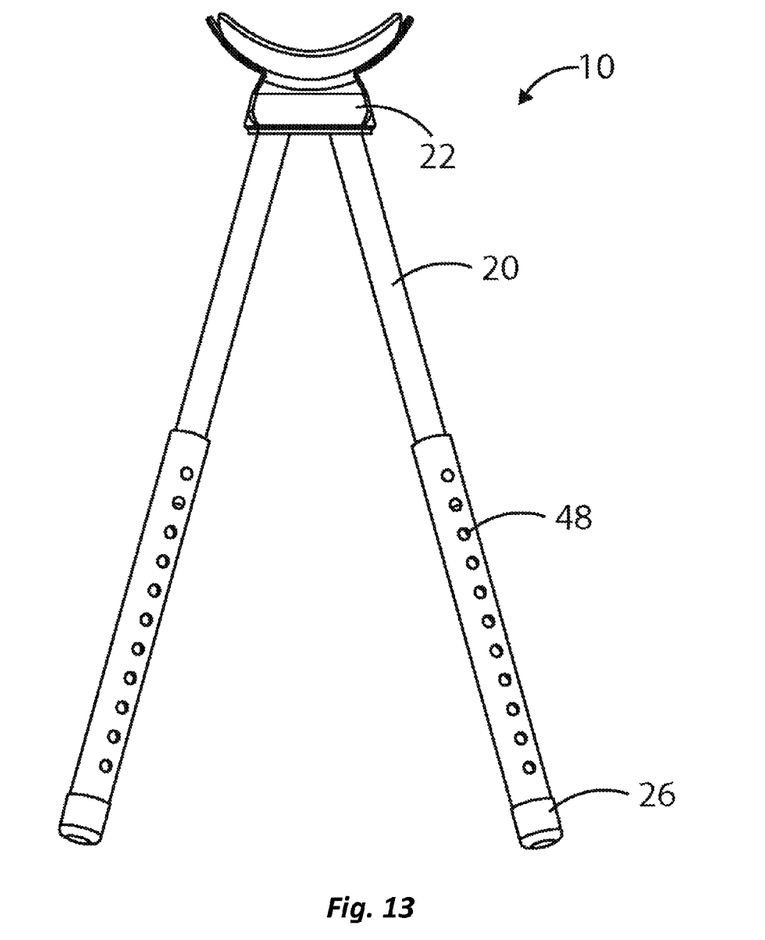
FIG. 13 is a top view of the preferred embodiment, illustrating a plurality of slots in the plurality of retracting leg members.

FIGS. 12 and 13 are a perspective view and top view, respectively, of the preferred embodiment, illustrating the plurality of leg members 20 in an extended position. The plurality of retractable leg members 20 utilizes the telescopic mechanism to adjust the height of the leg members 20. The plurality of retractable leg members 20 comprise a plurality of holes 48. The height of the plurality of retracting leg members 20 is adjusted utilizing the plurality of holes 48. Each of the plurality of leg members 20 has at least one hole-engaging button 46, as shown best in FIG. 12. In this mechanism, when the desired height is reached, one of the holes is engaged with the hole engaging button 46 on the leg members 20 such that the retracting leg members 20 will be locked at a set height, as is known in the art of telescoping legs.

Figure 14:
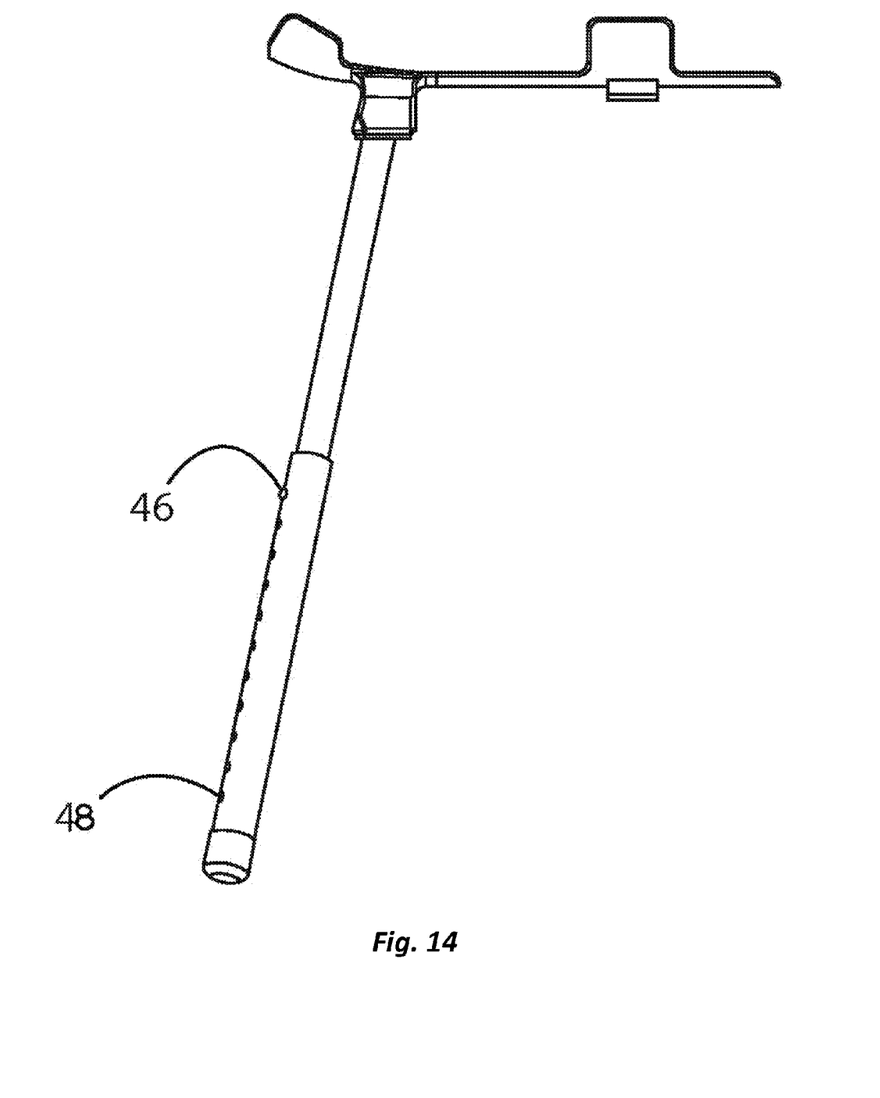
FIG. 14 is a side view of the preferred embodiment, illustrating at least one of the plurality of retractable leg members in an extended position.

FIG. 14 is a side view of the preferred embodiment, illustrating at least one of the leg members 20 in an extended position. The telescopic mechanism allows each of the leg members 20 to adjust the height independently thereby providing different heights to each of the leg members 20. Again a hole engaging button 46 is partially visible through one of said plurality of holes 48.

In alternative embodiments of the invention, the hinges may be slidably connected to the rear surface such that they are longitudinally slidable up and down. In still other embodiments the leg support device may be manufactured as a permanent component of an orthotic boot or other footwear. That is, instead of being releaseably attachable to an orthotic boot or footwear (using for instance, hook and loop type fasteners), a boot manufacturer may choose to completely integrate the leg support device by making it a permanent or even structural component of the boot. In one example the base plate and the rear of a manufactured orthotic boot may be the same component. Here, the front surface of the base plate may be the inner rear wall of an orthotic boot, just behind the heel of the wearer. In this example the rear plate may be a very similar component, serving as a substrate for attachment of the remaining support component.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed description, but by the claims and the equivalents to the claims appended hereto.

I claim:

1. A leg support device adaptable to maintain a user's leg in an elevated position, the leg support device comprising:
    an elongate base plate comprising a front surface, a rear surface, a curved calf cup and a curved heel cup, and at least one connector for releaseably attaching said base plate to a user's leg or footwear;
    a plurality of elongate, hollow, retractable leg members rotatably coupled to the base plate by a plurality of hinges, and being rotatably operable between a deployed configuration wherein the leg members are aligned generally perpendicular to said elongate base plate and in a stored configuration wherein the leg members are aligned generally parallel with said elongate base plate;
    a locking mechanism associated with the plurality of leg members the locking mechanism releasably securing said leg members when said leg members are in either said deployed configuration or said stored configuration; and
    wherein said locking mechanism comprises a plurality of first hinge pockets into which said leg members may be slotted in said deployed configuration and a plurality of second hinge pockets into which said leg members may be slotted in said stored configuration, each of said plurality of hinges being integral with said plurality of first hinge pockets and said plurality of second hinge pockets.

2. The leg support device of claim 1 wherein in said deployed configuration said plurality of leg members are partially inserted into said plurality of first hinge pockets.

3. The leg support device of claim 1 wherein in said stored configuration said plurality of leg members are partially inserted into said plurality of second hinge pockets.

4. The leg support device of claim 1 wherein in said deployed configuration said plurality of leg members are partially inserted into said plurality of first hinge pockets, and wherein in said stored configuration said plurality of leg members are partially inserted into said plurality of second hinge pockets.

5. The leg support device of claim 1 wherein each of said plurality of first hinge pockets is a cavity, recess, or other suitable receptacle for nesting a portion of one of said plurality of leg members, and each of said plurality of second hinge pockets is a cavity, recess, or other suitable receptacle for nesting the same portion of one of said plurality of leg members.

6. The leg support device of claim 4 wherein each of said plurality of first hinge pockets is a cavity, recess, or other suitable receptacle for nesting a portion of one of said plurality of leg members, and each of said plurality of second hinge pockets is a cavity, recess, or other suitable receptacle for nesting the same portion of one of said plurality of leg members.

7. The leg support device of claim 1 wherein said locking mechanism is configured to lock and release solely by pivoting said plurality of leg members.

\* \* \* \* \*